United States Patent
Walker et al.

(10) Patent No.: US 10,441,428 B2
(45) Date of Patent: Oct. 15, 2019

(54) EARLY INTERVENTION KNEE IMPLANT DEVICE AND METHODS

(75) Inventors: Peter Stanley Walker, New York, NY (US); Joseph A. Bosco, Irvington, NY (US)

(73) Assignee: New York University, New York, NY (US)

(*) Notice: Subject to any disclaimer, the term of this patent is extended or adjusted under 35 U.S.C. 154(b) by 179 days.

(21) Appl. No.: 13/099,967

(22) Filed: May 3, 2011

(65) Prior Publication Data

US 2012/0116524 A1 May 10, 2012

Related U.S. Application Data

(60) Provisional application No. 61/330,682, filed on May 3, 2010.

(51) Int. Cl.
  *A61F 2/38* (2006.01)
  *A61B 17/15* (2006.01)
  *A61F 2/30* (2006.01)

(52) U.S. Cl.
  CPC .......... *A61F 2/3859* (2013.01); *A61B 17/155* (2013.01); *A61B 17/157* (2013.01); *A61F 2/389* (2013.01); *A61F 2002/30878* (2013.01); *A61F 2002/30884* (2013.01); *A61F 2002/30889* (2013.01); *A61F 2002/30891* (2013.01); *A61F 2002/30892* (2013.01); *A61F 2002/3895* (2013.01)

(58) Field of Classification Search
  CPC .................... A61F 2/3859; A61F 2/389; A61F 2002/3895; A61F 2002/30878; A61F 2/38; A61F 2002/3863

USPC .......................................... 623/20.14–20.36
See application file for complete search history.

(56) References Cited

U.S. PATENT DOCUMENTS 3,953,899 A * 5/1976 Charnley ...................... 623/20.3
4,034,418 A    7/1977 Jackson et al.
(Continued)

FOREIGN PATENT DOCUMENTS

FR         9614758 A  * 12/1996 .................. 623/20.29
WO    2010/042941 A2     4/2010

OTHER PUBLICATIONS

International Search Report for PCT/US2009/060484, dated Jun. 24, 2010 (4 pages).
(Continued)

*Primary Examiner* — Christopher D. Prone
(74) *Attorney, Agent, or Firm* — Kilpatrick Townsend and Stockton LLP

(57) ABSTRACT

A replacement knee implant has a femoral implant and a tibial implant, each of which are inset in a bone surface. The tibial implant is generally elongated with one end rounded and an opposite end conforming to the shape of the tibia, and is made of a metal alloy or a ceramic. The upper surface is dished while the lower surface is planar and can be parallel or sloped relative to the upper surface, and can have a keel for fixation. The femoral implant for implementation in a femoral condyle is rounded such that, when implemented, the femoral implant is flush at the anterior and posterior sides and protruding away from the femur between the anterior and posterior ends. The femoral implant can have an elongated keel for extending into the femur, and can be made from a highly cross-linked polyethylene.

23 Claims, 14 Drawing Sheets

(56) References Cited

U.S. PATENT DOCUMENTS

| | | | |
|---|---|---|---|
| 4,094,017 A | 6/1978 | Matthews et al. | |
| 4,224,696 A * | 9/1980 | Murray et al. | 623/20.29 |
| 4,340,978 A | 7/1982 | Buechel et al. | |
| 4,501,031 A | 2/1985 | McDaniel et al. | |
| 4,634,444 A | 1/1987 | Noiles | |
| 4,800,639 A | 1/1989 | Frey et al. | |
| 5,064,437 A | 11/1991 | Stock et al. | |
| 5,171,276 A | 12/1992 | Caspari | |
| 5,201,768 A | 4/1993 | Caspari et al. | |
| 5,312,411 A | 5/1994 | Steele et al. | |
| 5,871,546 A | 2/1999 | Colleran et al. | |
| 6,059,831 A | 5/2000 | Braslow et al. | |
| 6,206,927 B1 | 3/2001 | Fell et al. | |
| 6,558,421 B1 | 5/2003 | Fell et al. | |
| 6,652,588 B2 | 11/2003 | Hayes et al. | |
| 6,723,102 B2 | 4/2004 | Johnson et al. | |
| 6,783,550 B2 | 8/2004 | MacArthur | |
| 6,866,684 B2 | 3/2005 | Fell et al. | |
| 6,893,463 B2 | 5/2005 | Fell et al. | |
| 6,911,044 B2 * | 6/2005 | Fell | A61F 2/38 623/14.12 |
| 6,946,001 B2 | 9/2005 | Sanford et al. | |
| 6,966,928 B2 * | 11/2005 | Fell | A61F 2/38 623/14.12 |
| 7,033,397 B2 | 4/2006 | Webster et al. | |
| 7,105,027 B2 * | 9/2006 | Lipman et al. | 623/20.29 |
| 7,105,026 B2 | 12/2006 | Johnson et al. | |
| 7,258,701 B2 | 8/2007 | Aram et al. | |
| 7,297,161 B2 | 11/2007 | Fell | |
| 7,338,524 B2 | 3/2008 | Fell et al. | |
| 7,341,602 B2 | 3/2008 | Fell et al. | |
| 7,462,198 B2 | 12/2008 | Webster et al. | |
| 7,462,199 B2 | 12/2008 | Justin et al. | |
| 7,488,324 B1 | 2/2009 | Metzger et al. | |
| 7,491,235 B2 | 2/2009 | Fell | |
| 7,513,912 B2 | 4/2009 | Hayes, Jr. et al. | |
| 7,520,901 B2 | 4/2009 | Engh et al. | |
| 7,578,850 B2 | 8/2009 | Kuczynski et al. | |
| 7,608,079 B1 | 10/2009 | Blackwell et al. | |
| 8,682,052 B2 * | 3/2014 | Fitz | A61F 2/30756 382/128 |
| 8,882,847 B2 * | 11/2014 | Burdulis, Jr. | A61F 2/38 623/20.32 |
| 2002/0022889 A1 * | 2/2002 | Chibrac | A61F 2/3603 623/18.11 |
| 2003/0055501 A1 * | 3/2003 | Fell | A61F 2/38 623/14.12 |
| 2005/0171612 A1 | 8/2005 | Rolston | |
| 2007/0005142 A1 * | 1/2007 | Rhodes | A61F 2/389 623/20.32 |
| 2007/0299530 A1 | 12/2007 | Rhodes et al. | |
| 2008/0058945 A1 | 3/2008 | Hajaj et al. | |
| 2008/0119931 A1 | 5/2008 | Fell et al. | |
| 2008/0288080 A1 | 11/2008 | Sancheti et al. | |
| 2009/0125115 A1 * | 5/2009 | Popoola | A61F 2/38 623/20.14 |
| 2009/0183291 A1 | 7/2009 | McCall | |
| 2009/0228113 A1 | 9/2009 | Lang et al. | |
| 2009/0270995 A1 | 10/2009 | Rhodes et al. | |

OTHER PUBLICATIONS

International Search Report for PCT/US2011/034988, dated Oct. 4, 2011 (4 pages).

* cited by examiner

EARLY INTERVENTION KNEE IMPLANT DEVICE AND METHODS

CROSS-REFERENCE TO RELATED APPLICATIONS

This application claims priority under 35 U.S.C. Section 119(e) to Provisional Application Ser. No. 61/330,682, filed May 3, 2010, the entirety of which is hereby incorporated herein by reference.

FIELD OF THE INVENTION

This disclosure relates to orthopedic knee implants, e.g., for the treatment of osteoarthritis (OA) and degenerative disorders of the knee joint at a relatively early stage in the disease process.

BACKGROUND

The earliest implants for the treatment of OA of the knee consisted of fixed metallic hinges at one extreme, and some type of interposition at the other extreme. Interpositions included the use of fascia and other 'soft' biological materials, and also metallic tibial plateaus and metallic shells covering the distal femoral condyles. The 'soft' materials could fail due to inadequate strength and the lack of fixation to the bone. The metallic components fared better. Tibial plateaus, such as those in designs known as Macintosh and McKeever designs, served to space apart the bearing surfaces, thus potentially correcting the deformity, and provided a smooth bearing surface for the femoral condyles. Lack of fixation of the Macintosh implant to the tibia sometimes allowed movement or even dislocation, in the McKeever design, the use of keels prevented this problem. The femoral resurfacing devices faced the dual problem of matching the surface geometry of the original intact femur, and of shaping the distal femur to fit the implant. It is believed that obtaining a satisfactory range of motion, as well as stability, would be a problem in many cases due to the geometrical factors noted above. Another issue with such devices, which were not rigidly fixed to the bone, was that there would be 'interface micromotion' leading to resorption of the adjacent bone and replacement with fibrous tissue, leading to residual pain or aching.

This experience with interposition devices pointed to the benefits of rigid fixation of the device to the bone, and to geometrical compatibility within the joint. The question of whether pain resulted from the lack of fixation, or from the opposite side of the joint articulating with a rigid metal surface, was not clear. Clues to that question came from the hip, following the use of Austin-Moore implants for replacement of the femoral head. There was still some residual pain from uncemented femoral components, but far less when the components were cemented. There does not seem to have been a series of knees where a McKeever or a similar device has been fixed to the upper tibia using cement or other means, hence the source of the pain remains in some doubt in the knee. Another question with the use of an interposition device in the knee is the potential wearing away of the cartilage (or even bone) on the opposite side; because the rigidity of the metal caused the contact stresses to be elevated. In the case of a medial metallic tibial plateau, for a shallow bearing surface, the stresses would be significantly elevated, because in the intact knee, the meniscus would spread the load over a wide area. This fact suggests that the cartilage on the medial femoral condyle could wear out more quickly than in a normal healthy joint.

An implant design of interest was the Gunston, designed in the late 1960's by Frank Gunston from Winnipeg while working as a Fellow at John Charnley's Hip Center in Wrightington, England. A metal half-disc is embedded in the femoral condyle and just projects from it, and is articulated on a plastic runner set into the medial plateau. There was almost complete conformity in the frontal plane, and partial conformity in the sagittal plane.

This configuration had several benefits. The sagittal curve of the femoral condyle could be fairly closely reproduced given sufficient sizes, the slot in the femoral condyle gave a large surface area of strong cancellous bone for cemented fixation, and the tibial surface provided a combination of AP and rotational stability and laxity.

The negatives were that a single sagittal femoral radius could not reproduce the reduced radius in high flexion and the increased radius in extension at the distal end of the femur, cutting a slot in the femoral condyle sometimes endangered the strength of the bone on the outside, and the tibial plateau was of insufficient surface area such that sinkage and loosening occurred, and uncovered bone often impinged on bone on the opposite condyle or abraded against the plastic.

The polycentric knee, as it became known, was used in thousands of cases, especially at the Mayo Clinic, and provided good clinical results in a high percentage of cases.

In the early 1970's, Charnley produced an alternative implant, as shown, for example, in U.S. Pat. No. 3,953,899. Charnley used a thin flat metal plate with a single inner keel for fixation. This approach preserved of most of the strong cortical and sclerotic bone on the upper tibia to maximize the fixation, especially important for a component which did not necessarily cover the entire surface of the medial condyle. However it was difficult to position the flat plate so that it was in line with the force vector, which would result is some shear instability in some cases. Charnley also designed a plastic runner that was embedded into the distal femur. The name 'Load-Angle Inlay' (LAI) described this particular feature of Charnley's implant. The plastic runner was set so that it projected about 2 mm from the surrounding surface but was made to be flush at the anterior and posterior. This arrangement, where the plastic surface was convex and the metal surface was flat, was opposed to the convention of metal-plastic bearings, where the stationary and concave (or flat) component should be plastic and the moving surface metal. The rationale being that the stresses in the convex plastic would be higher potentially leading to delamination wear, and the plastic might wear unevenly which, in the extreme, might cause a discontinuity in the knee motion.

In practice, wear testing would be needed to determine whether the particular configuration used in the Charnley LAI would function well enough for its application, although there appears to be no public records in leading literature for such testing. Minns, Day, and Hardinge (1982) carried out a motion analysis of 29 patients, which indicated satisfactory function, with no mechanical problems being reported.

Another type of knee for medial OA was the unicompartmental or 'uni', introduced in the early 1970's. This design consisted of a metal femoral runner onlaid over the entire arc of the femoral condyle from extension to full flexion. The component design varied from having a curved undersurface to contact the femoral bone after removing any residual cartilage, to a facetted surface requiring flat cuts to be made with an osteotome or saw. The fixation was usually augmented with one or more posts, or blades, or a combination, using cement for immediate and long-term fixation. The tibial component consisted of a hemicircular disc of plastic, sometimes fitting inside a metallic baseplate. The baseplate helps prevent deformation of the plastic in the short and long-term, and the fixation to the bone was more durable. One disadvantage is that more tibial bone needs to be removed to account for the metal, paradoxically having an adverse effect on the fixation due to the fact that the strength of the cancellous bone in the proximal tibia diminishes with depth. As with the femoral component, fixation was by cement, and the undersurface had a combination of posts or blades. On all designs, the upper tibial surface has been close to flat, providing little AP stability, in contrast to the medial surface of the intact knee. This round on flat, or at best cylinder on flat, configuration produces high contact stresses. In long-term follow-ups, for net-shape molded polyethylene, there has typically been a trough formed due to wear and deformation, but no delamination.

An alternate design has been the meniscal bearing uni, where the femoral component had a spherical bearing surface, with the back surface being faceted. The tibial component consisted of a flat metallic plate with a polished upper surface. A plastic meniscus was interposed between the two components and conformed with each. This produced low contact stresses, which minimizes deformation and wear. There was no constraint to AP displacement, other than friction.

The following refers to a study carried out in one of the inventors' laboratory, on the nature of the osteoarthritic lesions at the time of total knee replacement surgery. One of the main purposes of the study was to determine if an early intervention procedure could have been carried out involving only replacement of the medial side of the joint, rather than a total knee. The study of 100 cases was reported to the Orthopaedic Research Society's Annual Meeting in 2007. The predominant lesion of the medial femoral condyle was distal, which is the region which undergoes weight-bearing in walking, by far the most frequent activity of everyday living. The posterior condyle on the other hand was frequently preserved, which makes sense because it is only weight-bearing in the less frequent high flexion activities such as rising from a chair and steep stair climbing. The lateral condyle was usually intact by visual appearance. A later study where the lateral histology was examined, showed that the cartilage structure was normal for that age group of individuals.

On the tibial side, the lesion on the medial plateau varied in location. On the other hand, the lateral side showed normal cartilage on that area covered by the meniscus, but cartilage with some softening and fibrillation on the area not covered by the meniscus. Hence the medial side showed degeneration where a repair was necessary, while the lateral side was frequently normal such that it could sustain normal weight-bearing without need of replacement.

Most of the lesions occurred within the anterior half, the central half, or extended more than one half. A lesser number involved the posterior. When all of the lesions for all 100 cases were superimposed, it was seen that all of the medial tibial plateau could be involved. This indicated that if a single style of tibial component was designed, it would need to cover substantially the whole of the tibial plateau.

SUMMARY

In one aspect, the invention provides for a femoral resurfacing implant. The implant has a substantially rectangular perimeter and a length and width approximating a section of resected femoral condyle. It has a bearing surface having a substantially biconvex morphology conforming generally to the curvature of the femoral condyle. The femoral implant in various embodiments has one or more fixation structure, which may include pegs or a keel. In another embodiment, the fixation structure is trabecular metal fused to a portion of the implant. In other embodiments, the femoral implant is ultra-high molecular weight polyethylene, highly cross-linked ultra-high molecular weight polyethylene, polyetheretherketone, and/or polyurethane.

In another aspect, the invention provides for a tibial resurfacing implant. The implant has a structure that is substantially planar, relatively elongated in the x and z axes, but relatively thin in the y axis, and having a perimeter defined by at least one substantially straight side, with the remaining perimeter being relatively annular and conforming substantially to a perimeter of a tibia. The implant has a femoral-facing surface and a tibial-facing surface, the femoral-facing surface characterized by a dished morphology and having intercondylar eminence; and a keel extending from the tibial-facing surface, the keel substantially parallel to the substantially straight side. In one embodiment, the tibial-facing implant surface tapering or angled relative to the keel. In another embodiment, the keel includes a cylindrical portion extending from an anterior end of the keel to a posterior end of the keel, the diameter of the cylindrical portion at the anterior end of the keel approximating the diameter of the cylindrical portion at the posterior end of the keel. In various embodiments, the tibial-facing surface tapers downward medially in the frontal plane; or the tibial-facing surface angled downward posterior in the sagittal plane; or a combination of both conformations. In other embodiments, the implant is a one-piece unit. In still other embodiments, the medial thickness of the planar component is increased in one or more regions conforming to a medial slope of a resected tibial surface. In other embodiments the tibial-facing surface is substantially flat. In still other embodiments the tibial-facing surface is textured. In even yet other embodiments, the cylindrical portion has annular notches or extrusions, for example but not limited to having annular notches or extrusions between 0.1 and 0.2 mm relative to the diameter of the cylindrical portion. In particular embodiments, the diameter of the cylindrical portion at the anterior end of the keel is greater than the diameter of the cylindrical portion at the posterior end of the keel. In certain embodiments, a distance between the tibial-facing surface and cylindrical portion at the posterior end of the keel is greater than a distance between the tibial-facing surface and the cylindrical portion at the anterior end of the keel. In certain other embodiments, the a difference between the distance between the tibial-facing surface and cylindrical portion at the anterior end of the keel and the distance between the tibial-facing surface and the cylindrical portion at the posterior end of the keel is between about 0.2 mm and 0.5 mm. In one embodiment, the tibial implant has a thickness of 5 mm or less at its thinnest point along the y axis of the structure. In another embodiment, the tibial implant varys in thickness at one or more regions said variation conforming to the slope of a tibial bone resection area in frontal or sagittal planes, for example but not limited to a slope of the tibial bone resection in the frontal plane between about 3 and about 8 degrees or a slope of the tibial bone resection in the sagittal plane between about 3 and about 8 degrees, or with sloping in both planes. In various embodiments, the tibial implant is cobalt chrome alloy, titanium alloy or ceramic, and may include one or more coated regions.

In another aspect, the invention provides for a knee implant set, including in combination, a femoral implant and a tibial implant.

In another aspect, the invention provides for a tibial surgical cutting guide. This tibial surgical cutting guide includes a cutting block having a bone-facing surface substantially conforming to the anterior of a tibia, the cutting block defining a plurality of through holes and a plurality of fixation holes, the through holes and fixation holes oriented substantially perpendicular to the bone-facing surface, the cutting block further defining a slot sized to accept a surgical saw blade or burr; two or more guide pins having a diameter that corresponds to the diameter of the through holes and a length that extends through the cutting block and spans a proximal tibial surface, the orientation of the pins aligning the cutting block on the tibia in both frontal and sagittal planes; and at least two fixation pins having a diameter that corresponds to the diameter of the fixation holes, the fixation pins securing the cutting block to the tibia once the guide pins have oriented the cutting block. In one embodiment, the cutting block slot is offset from the through holes at a distance that substantially corresponds to the thickness of a tibial resurfacing implant, for example but not limited to an offset of about 3 mm or less.

In another aspect, the invention provides for a femoral surgical cutting guide set. The femoral surgical guide set includes a first frame having a substantially rectangular perimeter approximating an area of a femoral lesion and a brace across the width of the first frame defining posterior and anterior burr-hole cavities, the brace defining a plurality of guide holes and a central fixation hole; a first screw having a diameter corresponding to the central fixation hole; a plurality of rotational security pins having diameters corresponding to the guide holes; a second frame having a perimeter substantially equal to the first frame, the second frame defining an anterior fixation hole, a posterior fixation hole, and a central burr-hole cavity; a second fixation screw corresponding to the diameter of the anterior fixation hole and a third fixation screw corresponding to the diameter of the posterior fixation hole. In one embodiment, the burr hole cavities have substantially rounded corners. In another embodiment, the diameter of the rotational security pins is about 2 mm. In yet another embodiment, the diameter of at least one burr-hole cavity is between 6 mm and 12 mm.

In another aspect, the invention provides for a knee implant set, including in combination, a femoral surgical cutting guide set and a tibial surgical cutting guide.

In another aspect, the invention provides for a kit having a knee implant set. The knee implant set includes in combination, a femoral implant and a tibial implant with instructions for use, in sterile packaging. The kit includes in various embodiments, a tibial surgical cutting guide and a femoral surgical cutting guide set. In other embodiments, the kit includes one or more surgical cutting devices, for example but not limited to a ball-end burr, such as surgical burrs between 6 mm and 12 mm in cutting diameter, such as a 9 mm burr.

In yet another aspect, the invention provides for surgical methods for knee resurfacing in a patient having a degenerative knee condition, using the above implants and cutting guides. In such methods, the surgeon undertakes resurfacing a femur in the patient by removing a portion of condyle surface to create a resected femoral condyle; affixing in the resected femoral condyle a femoral implant, the femoral implant comprising a femoral-resurfacing component and a bone fixation structure, the resurfacing component bearing surface substantially conforming in vivo to the morphology of a native, healthy femoral condyle in the patient; resurfacing the tibia in the patient by resecting a portion of the tibia; and affixing in the resected portion of the tibia a tibial implant. In one embodiment, the resurfacing step includes affixing a first frame to the condyle, the first frame having a substantially rectangular perimeter approximating an area of a femoral lesion and a brace across the width of the first frame defining a posterior burr-hole cavity and an anterior burr-hole cavity, the brace defining a plurality of guide holes; inserting a plurality of rotational security pins in the plurality of guide holes; burring the femoral bone accessible through the anterior and posterior burr-hole cavities to a resected depth; removing the first frame and affixing a second frame having a perimeter substantially equal to the first frame to the condyle, the second frame defining a central burr-hole cavity; burring the femoral bone accessible through the central burr-hole cavity to the resected depth, the femoral bone accessible through the central burr-hole cavity previously occluded by the brace of the first frame; and burring fixation holes in the femoral bone to a fixation hole depth through the anterior and posterior burr holes. In one embodiment, before the resurfacing step the patient's knee is imaged to locate and determine the extent of the degeneration and to create three-dimensional maps of the femoral and tibial surfaces of the patient. In other embodiments, the resurfacing step further includes affixing a cutting block having a bone-facing surface substantially conforming to the anterior of a tibia, the cutting block defining a plurality of through holes a slot sized to accept a surgical saw blade or burr, the through holes oriented substantially perpendicular to the bone-facing surface; aligning the cutting block on the tibia in both frontal and sagittal planes by inserting one or more guide pins having a diameter that corresponds to the diameter of the through holes and a length that extends through the cutting block and spans a proximal tibial surface, and resecting a portion of the tibia through the slot of the cutting block. In one embodiment, the tibial implant is affixed to the tibia by cementing with a surgical bone cement preparation. In another embodiment, the tibial implant is affixed to the tibia by one or more features on the tibial bone facing surface, without cementing. In another embodiment, the femoral and tibial implant resections substantially preserve surrounding healthy tissue. In still other embodiments, the tibial implant resection does not exceed 5 mm in depth.

In still another aspect, the invention provides for a method of making a patient-specific knee implant set. This method includes imaging the knee of a patient having a degenerative knee condition thereby creating one or more three-dimensional maps of the femoral and tibial surfaces of the patient; providing the femoral and tibial maps to a computer system, the computer system having software for rendering the femoral and tibial maps into a 3-dimensional virtual model of the femur and tibia of the patient; determining femoral and tibial subregions defining femoral and tibial implant locations from the virtual model; creating a femoral and/or a tibial implant from the virtual model of the femoral and tibial implant locations such that the exterior surfaces of the femoral and/or the tibial implant substantially conforms to the shape of a native femoral condyle or a native tibial surface, respectively; the femoral implant further comprising a bearing surface with a substantially biconvex morphology, and the tibial implant further comprising a dished morphology and intercondylar eminence and a keel extending from the tibial-facing surface, the keel substantially parallel to the substantially straight side. In one embodiment, the method includes creating a patient-specific tibial surgical cutting guide or a patient-specific femoral surgical cutting guide set from the 3-dimensional virtual model.

Other features and advantages will become apparent from the following description, drawings, and claims.

BRIEF DESCRIPTION OF THE DRAWINGS

These embodiments and other aspects of this invention will be readily apparent from the detailed description below and the appended drawings, which are meant to illustrate and not to limit the invention, and in which.

DESCRIPTION

Disclosed herein are knee implant devices, surgical cutting guide sets and methods for providing knee resurfacing implants to human patients having degenerative disorders of the bones and soft tissues of the knee, such as osteoarthritis and mechanical wear due to aging. The implant devices include femoral implants and tibial implants, each of which has novel features and aspects. Each of the various devices and their features and uses will be described in turn, and specific embodiments are presented by the figures, which are exemplary only and not meant to be limiting.

Figure 1:
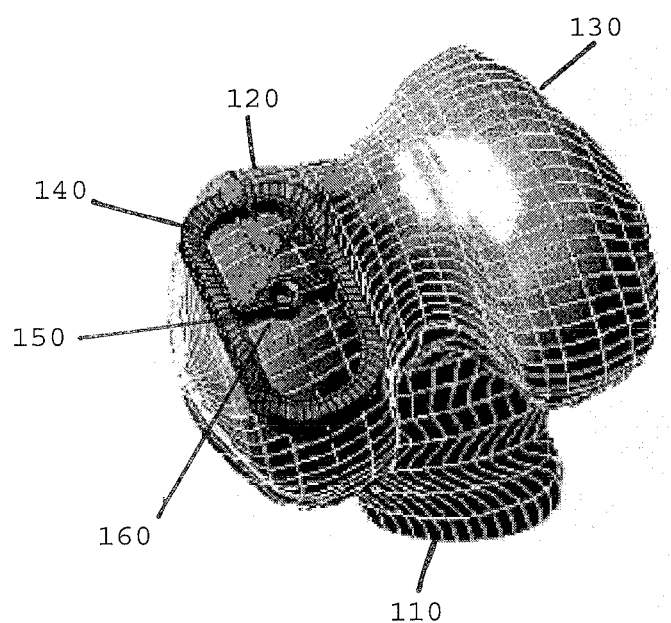
FIG. 1 illustrates installation of a first frame portion of a surgical guide on a femoral condyle in accordance with an embodiment of the invention.

Turning now to the figures, FIG. 1 illustrates a femur 110 having a medial condyle 120 and a lateral condyle 130. In this illustration the medial condyle 120 is prepared for resurfacing by first removing bone and soft tissues, in preparation for placing a femoral resurfacing implant. To create precise cuts in the femur, a first surgical cutting guide is affixed to the medial condyle 120 of the femur, selecting a cutting guide size that best fits both the area of cartilage loss, and the femoral curvature. The first surgical cutting guide comprises a frame 140 having a substantially rectangular perimeter. As shown, the frame 140 is rounded on the inside corners, thereby permitting removal of bone and connective tissues when using a rounded surgical burr. Spanning the width of the frame 140 is a brace 150 defining a posterior and an anterior cavity, the brace having a central fixation hole 160. The brace 150 may further include one or more securing features (not visible in this example) such as extrusions or pins, that extend from the brace 150 portion of the frame 140, into guide holes previously formed into the condyle by the surgeon. The pins are sized such that they are of sufficient length and diameter to minimize movement of the cutting guide from rotational or lateral forces that may otherwise cause displacement of the first surgical cutting guide during removal of condyle tissue, which removal occurs within the posterior and anterior cavities of the guide. A pin diameter of about 2 milimeters or greater provides adequate structural stability. The surgical guide is positioned on the condyle such that the pins extend into the guide holes in the condyle, and the surgical cutting guide is removable secured to the condyle at the through hole 160 by a temporary fixation screw or similar removable fixation means. In using the first surgical cutting guide, after the surgeon removes femoral tissue within the guide, there will be a section of condyle remaining which was occluded by the bridge 150 portion. This occluded tissue includes the guide holes and fixation point, and will be removed in a subsequent cut, so if the pin and fixation screw lengths approximate the depth of the cuts in the condyle within the posterior and anterior cavities of the guide, the guide and fixation holes will be removed as well.

Figure 2:
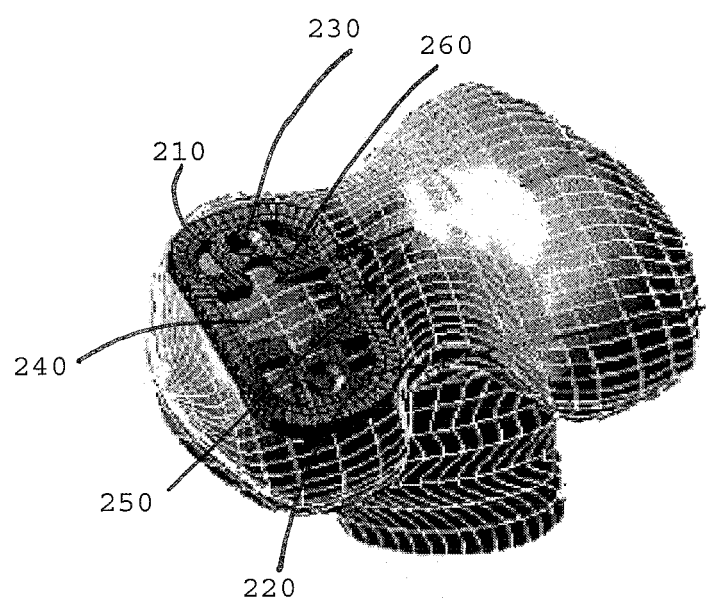
FIG. 2 illustrates installation of a second frame portion of a surgical guide on a femoral condyle in accordance with an embodiment of the invention.

A second surgical cutting guide is employed to finish preparing the implant site. This is illustrated in FIG. 2. A second surgical cutting guide permits removal of the condyle tissue occluded by the bridge 150 of the first surgical cutting guide. The second surgical cutting guide comprises a frame 210 having a perimeter substantially equal to perimeter of the first frame 150, the second frame defining an anterior fixation location 220 and an anterior guide 250 having a generally annular shape; a posterior fixation location 230 and a posterior guide 260; and a central cavity 240. The second surgical cutting guide is positioned on the femur such that the previously occluded portion of the condyle protrudes through the central cavity 240, and the second surgical cutting guide is removably secured to the femur by fixation screws corresponding to the diameter of the anterior fixation hole 220 and the posterior fixation hole 230. With the second surgical cutting guide in place, the surgeon removes condyle tissue in the central cavity 240 and creates fixation holes that extend into the inside surface of the condyle, which correspond in relative location to, and which will receive, the two reinforcing pins of a resurfacing component (not shown). The pins provide enhanced stability for the resurfacing component. These fixation holes are formed using the second surgical cutting guide at the anterior fixation location 220 and the posterior fixation location 230.

Figure 3:
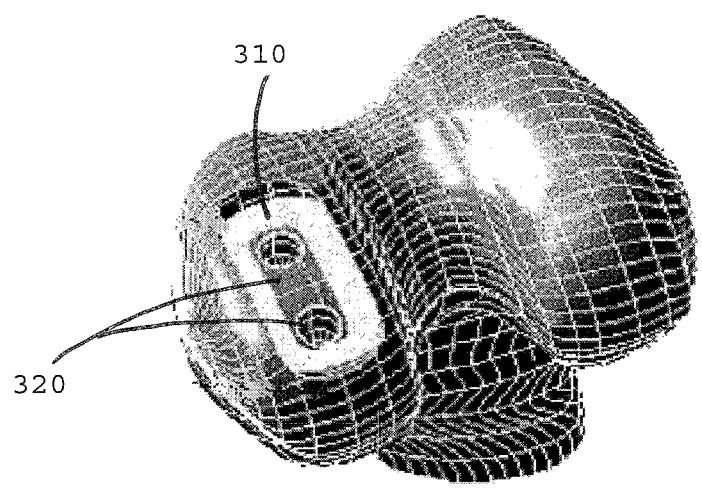
FIG. 3 shows a femoral pocket for receiving a femoral implant in accordance with an embodiment of the invention.

FIG. 3 shows a femur having a section of resected femoral condyle where a portion of the medial condyle has been removed. As illustrated, the femoral condyle was resected to create an implant site 310 having fixation holes 320 which correspond to extensions on a bearing surface component (not shown). The particular section of the femur to be resurfaced will dictate the amount of tissue that must be removed, and to the extent possible the surgeon preserves healthy bone and cartilage tissue. In this illustration, the femoral condyle has been resected in such a manner that an insertion pocket is created for the resurfacing component. To create the insertion site, standard surgical techniques are employed. For example, bone deburring is accomplished using a ball-end burr. In our example, a burr having a 9 mm diameter is suitable although any diameter from 4 mm to 12 mm is reasonable, in the discretion of the surgeon. The stem of the burr has a plastic cylindrical sleeve over the burr, reaching down to the mid-diameter. Above the sleeve is a plastic washer of sufficient diameter so that it strides the frame even when the burr is against the inside of the frame at the side. The depth from the bottom of the washer to the tip of the burr is such that the total depth of cut into the condyle matches the implant. The burring tool, mounted on a rotating drill, is worked around the inside of the frame until all exposed areas are smoothed. The first surgical cutting guide is removed, and the process repeated using the second surgical cutting guide.

Figure 4:
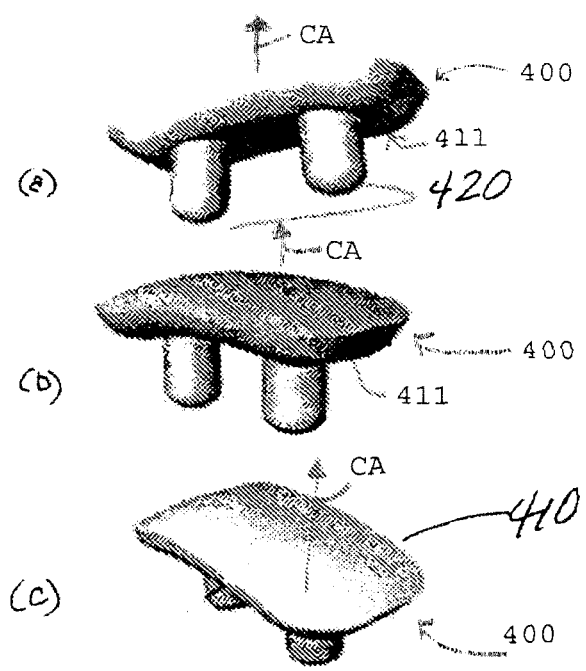
FIGS. 4(a)-(c) show perspective views of the femoral resurfacing implant in accordance with an embodiment of the invention.

FIG. 4 illustrates the resurfacing component of the device, in three views. The exterior bearing surface 510 of the resurfacing component is biconvex, and is designed to resurface areas of the femur that are commonly worn, e.g. due to osteoarthritis. The specific shape of the bearing surface and the degree of curvature in two dimensions is a function of the general shape of a healthy condyle surface in the recipient patient and the specific section of the condyle being resurfaced. As shown, the resurfacing component includes a bearing surface 410 that is approximately 7 mm thick and further includes one or more fixation structures 420 for stability. As illustrated, FIG. 4 shows two fixation structures in the form of pins.

Figure 5:
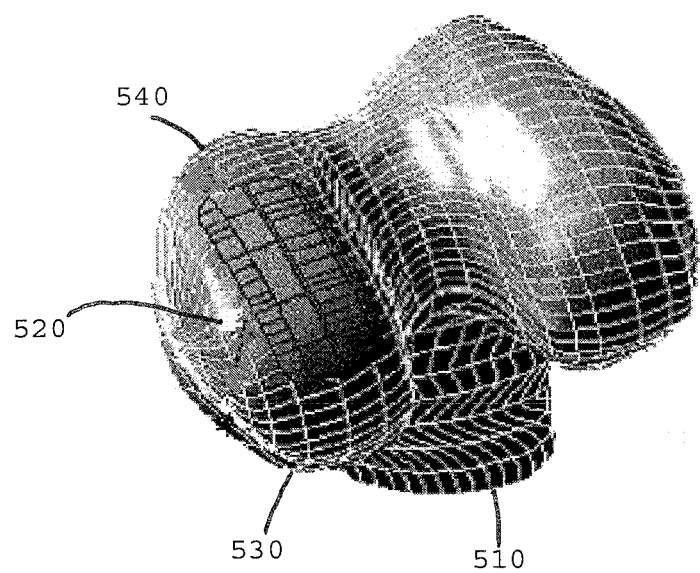
FIG. 5 illustrates installation of the femoral resurfacing implant in accordance with an embodiment of the invention.

FIG. 5 shows the femur 510 after placement of the femoral resurfacing component 520. The resurfacing component is surrounded by healthy tissue. As shown, the device is set in place such that exterior surface of the resurfacing component is flush with the cartilage at the anterior 530 and posterior 540 of the implant site. Close tolerances are achieved with the first and second surgical cutting guides, which permit accurate resection of the desired femoral condyle prior to implantation of the resurfacing component. In the case of a cemented resurfacing component, an exact match between the peripheral shape of the implant site and the implant component is not critical. However, the depth of the implant site is used to achieve a close or "flush" fit between the implant and condyle surface at the anterior and posterior of the implant site. Notably, it is useful to have a small protrusion of the resurfacing component midway between the anterior and posterior. A protrusion of about one millimeter at the center is sufficient. In the case of an uncemented resurfacing component, closer tolerances are useful. Here, deliberate undersizing of the resected implant site relative to the periphery of the implant component (e.g., less than 0.5 mm) achieves a tight fit following implantation.

Figure 6:
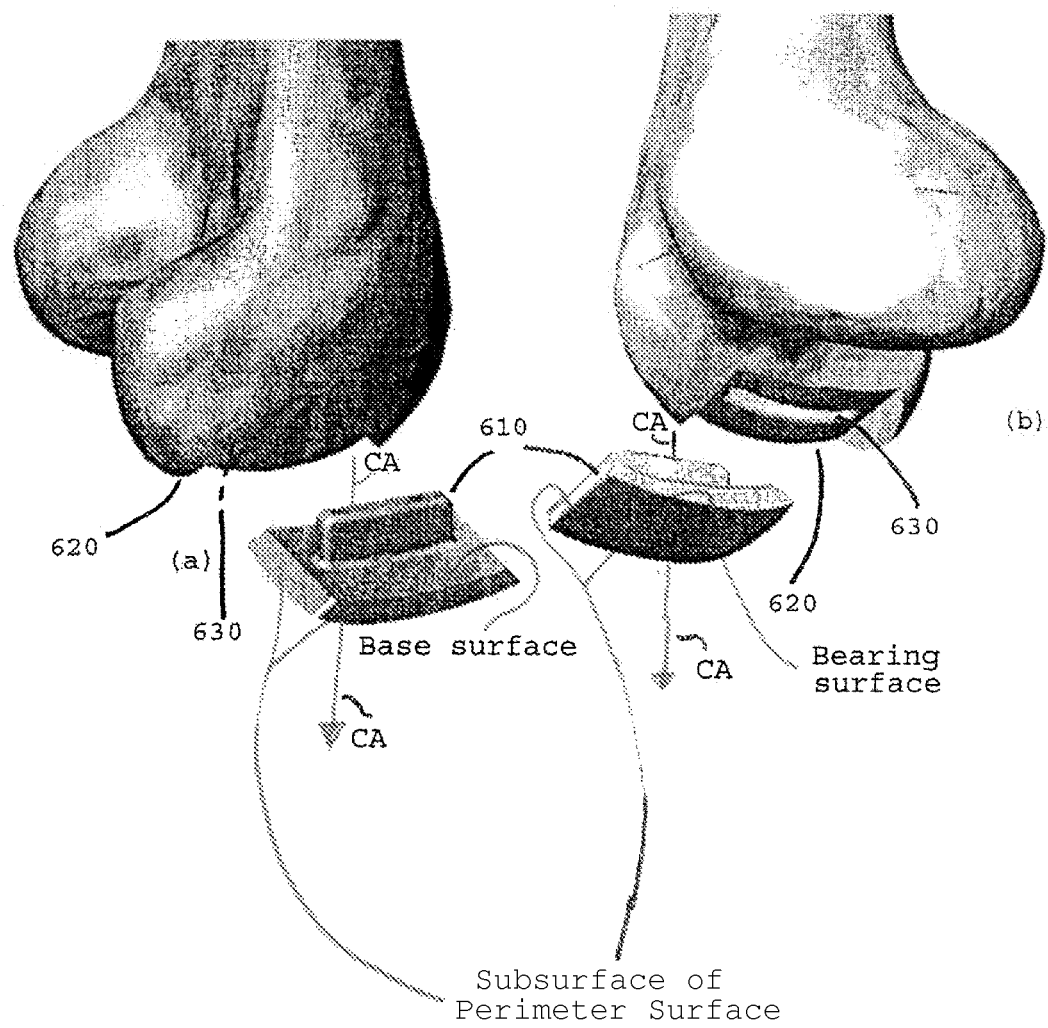
FIGS. 6(a)-(b) show an alternative femoral resurfacing implant in accordance with an embodiment of the invention.

FIG. 6 shows an alternative embodiment of the femoral resurfacing component. In this view, the fixation structure is provided as a keel feature 610. The insertion site 620 displays a single elongated trench-like fixation point 630.

Figure 7:
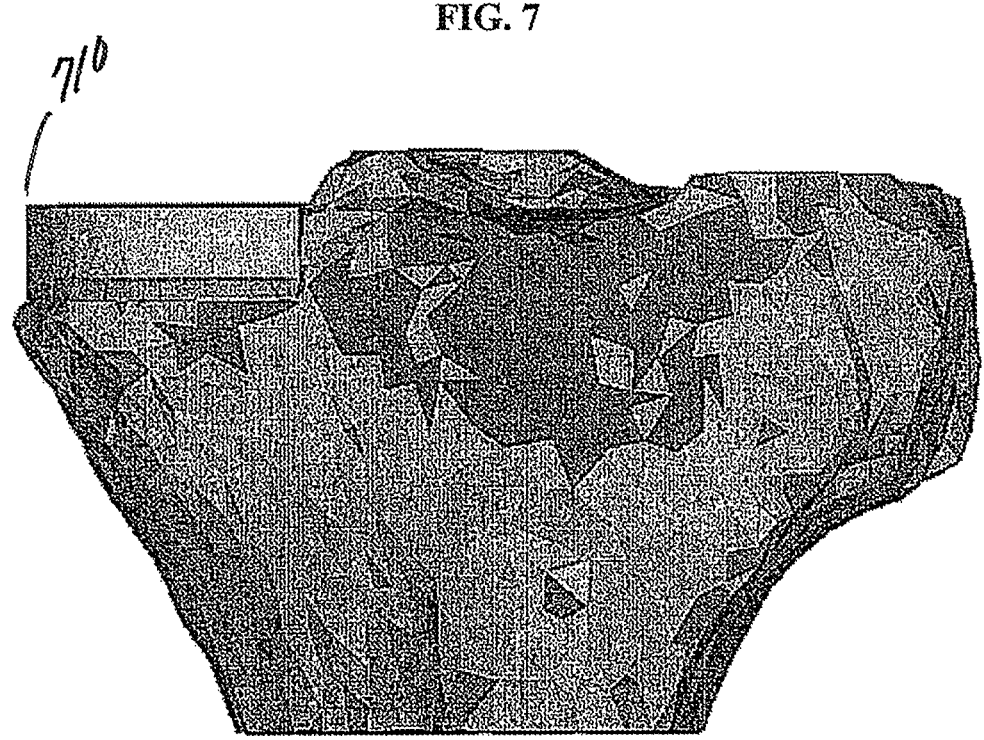
FIG. 7 illustrates a side-view of a traditional tibial implant.
Figure 8:
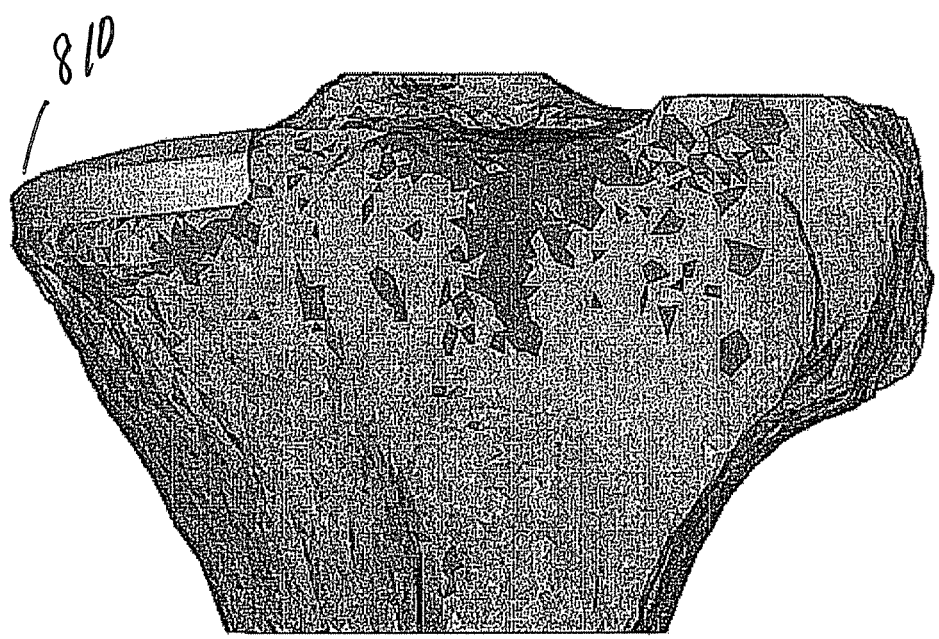
FIG. 8 illustrates a side view of a tibial implant in accordance with an embodiment of the invention.

The invention disclosed herein provides for both femoral implants as described and tibial implants, discussed in turn below. FIG. 7 illustrates a tibial resurfacing device of the prior art. As shown, the tibial implant has a well defined shoulder region 710 and is placed substantially parallel to the plane of the knee joint. In contrast, FIG. 8 illustrates an embodiment of the invention relating to a tibial component, where the implant has a sloping shoulder 810 and is substantially thinner. Notably, the placement is oriented in a manner that minimizes bone resection. Achieving precise resection of tibial tissue is accomplished using a tibial surgical cutting guide.

Figure 9:
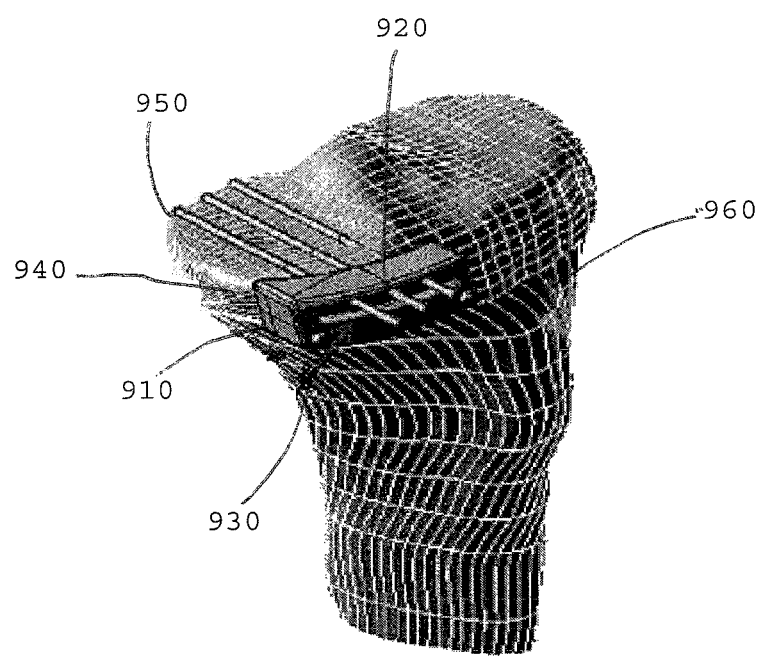
FIG. 9 illustrates a cutting block affixed to the anterior surface of a tibia in accordance with an embodiment of the invention.

FIG. 9 illustrates an embodiment of a tibial surgical cutting guide. The guide comprises a cutting block 910 having a bone-facing surface substantially conforming to the anterior of a tibia, the cutting block 910 defining a plurality of through holes 920 and a plurality of fixation holes 930, the through holes and fixation holes oriented substantially perpendicular to the bone-facing surface, the cutting block further defining a slot 940 sized to accept a surgical saw blade or burr. Guide pins 950 having a diameter that corresponds to the diameter of the through holes 920 and a length that extends through the cutting block and spans a proximal tibial surface, permit orientation of the cutting block on the tibia in both frontal and sagittal planes. Fixation pins 960 having a diameter that corresponds to the diameter of the fixation holes 930, secure the cutting block to the tibia. The cutting block 910 is positioned along the face of the tibia perpendicular to the knee joint. Guide pins 950 extend through the cutting block 910 and permit alignment of the cutting block on frontal and saggital planes, which can also be placed such that the cut is angled thereby preserving healthy bone tissue. Once positioned, the cutting block 910 is removably secured to the tibia and the surgeon can resect bone through the slot 940.

Figure 10:
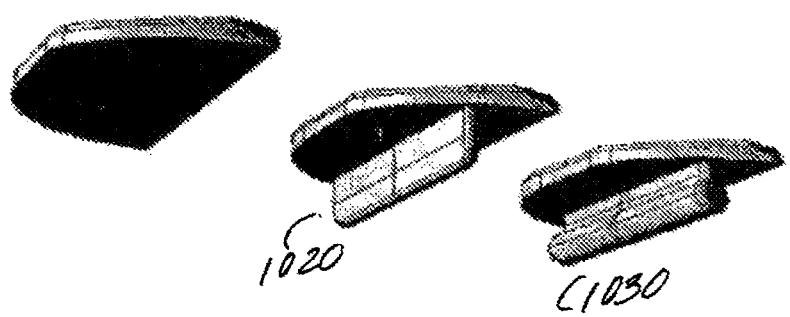
FIGS. 10(a)-(f) depict perspective views of various tibial implants in accordance with an embodiment of the invention.
Figure 10:
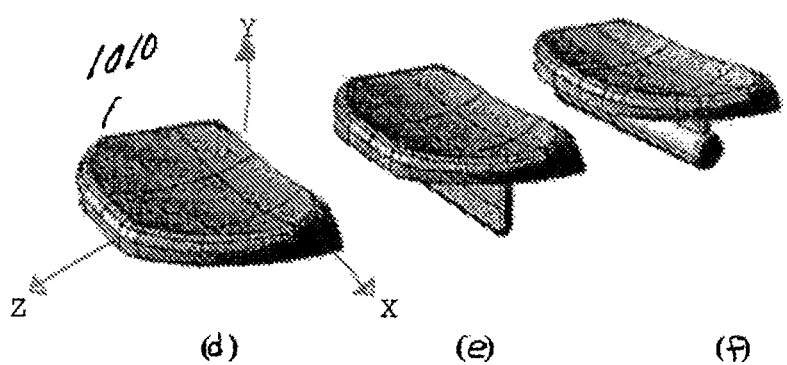

FIG. 10 shows in six views, three embodiments of the tibial component of the implant device. A tibial implant, comprises a structure that is substantially planar, relatively elongated in the x and z axes, but relatively thin in the y axis, and having a perimeter defined by at least one substantially straight side, with the remaining perimeter being relatively annular and conforming substantially to a perimeter of a tibia. The implant has a femoral-facing surface and a tibial-facing surface, the femoral-facing surface characterized by a dished morphology and having intercondylar eminence. The basic shape of the tibial component 1010 substantially conforms to the tibial area to be resurfaced, and the intercondylar eminence and double-dished surfaces provide anterior-posterior and medial-lateral stability. The device is illustrated as a 2 mm metal plate, which is a suitable thickness for providing structural rigidity to the device and at the same time, minimizing the amount of bone tissue that need be removed by the surgeon. The proximal region of the tibia provides for relatively stronger bone tissue as compared to more distal regions of the tibia, and so a shallower insertion pocket provides better strength at the interface of the tibia and the device. In alternative embodiments, a keel 1020 extends from the tibial-facing surface, the keel 1020 substantially parallel to the substantially straight side. The keel may have a cylindrical portion 1030 extending from an anterior end of the keel to a posterior end of the keel. The keel and keel-cylinder embodiments are for applications where the device is cemented or affixed without cementing, respectively.

Figure 11:
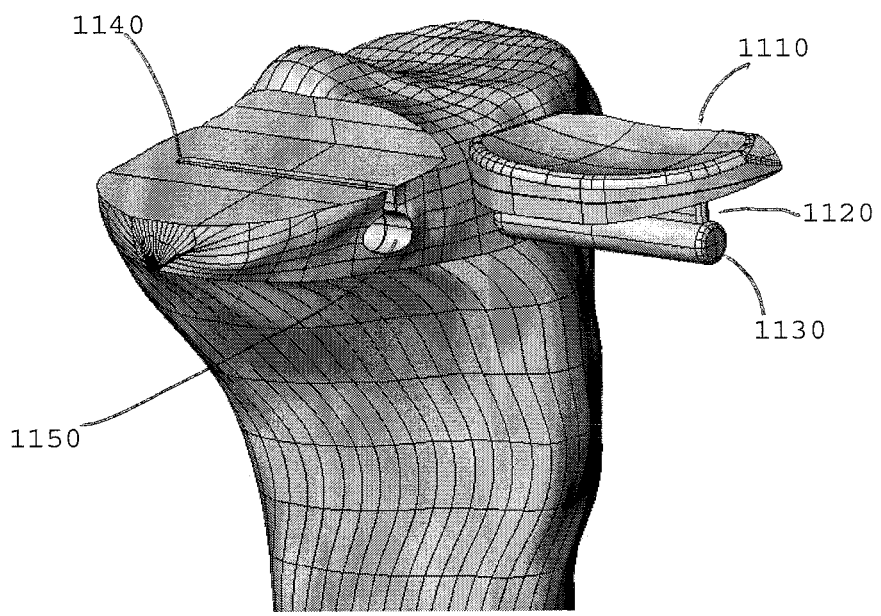
FIG. 11 depicts a resected tibia and tibial implant prior to insertion in accordance with an embodiment of the invention.
Figure 12:
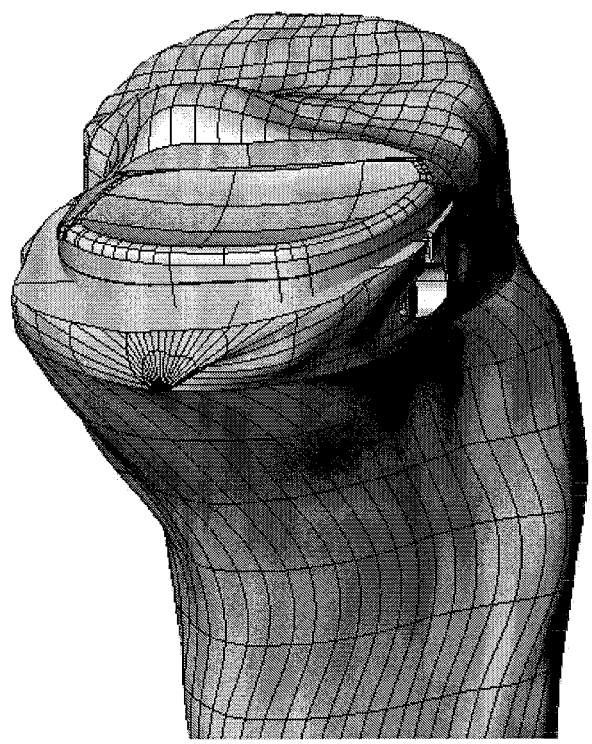
FIG. 12 illustrates a perspective view of a resected tibia and tibial implant after placement in accordance with an embodiment of the invention.
Figure 13:
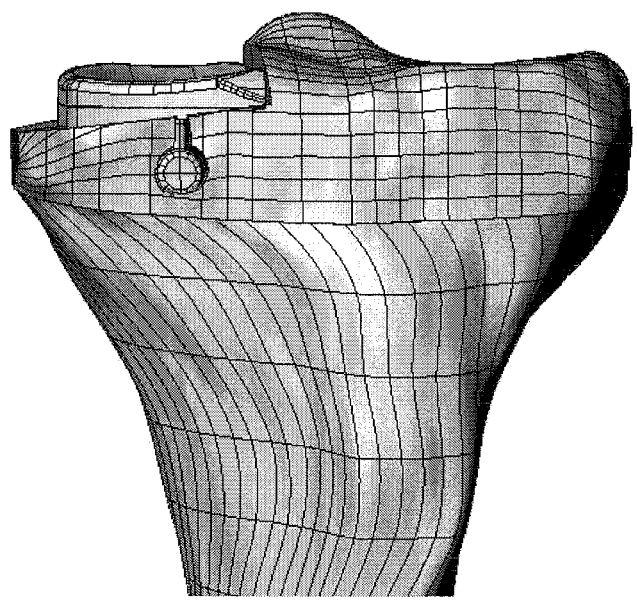
FIG. 13 illustrates a side view of a resected tibia and tibial implant after placement in accordance with an embodiment of the invention.

FIG. 11-13 show a resected tibia before and after placement of the tibial implant component. As illustrated in FIG. 11, the resected tibia has a generally D-shape portion that is removed to create the implant site. The particular tibial implant 1110 to be used has a keeled 1120 structure terminating with a cylindrical fixation feature 1130. Accordingly, the implant site has a groove 1140 that accommodates the keel and an aperture 1140 running the length of the groove and substantially parallel thereto, that accommodates the cylindrical fixation feature 1150. As illustrated, the implant has a dished upper surface to provide anterior-posterior (AP) stability and to reduce contact stresses. The tibial insert may be formed in one of several different ways, depending on whether there is a small or larger varus (bow-legged) deformity. As shown, the tibial component displays 5 degrees of frontal slope (varus tilt) and 7 degrees of saggital slope. FIGS. 12 and 13 illustrate the implant in position in the tibia.

Figure 14:
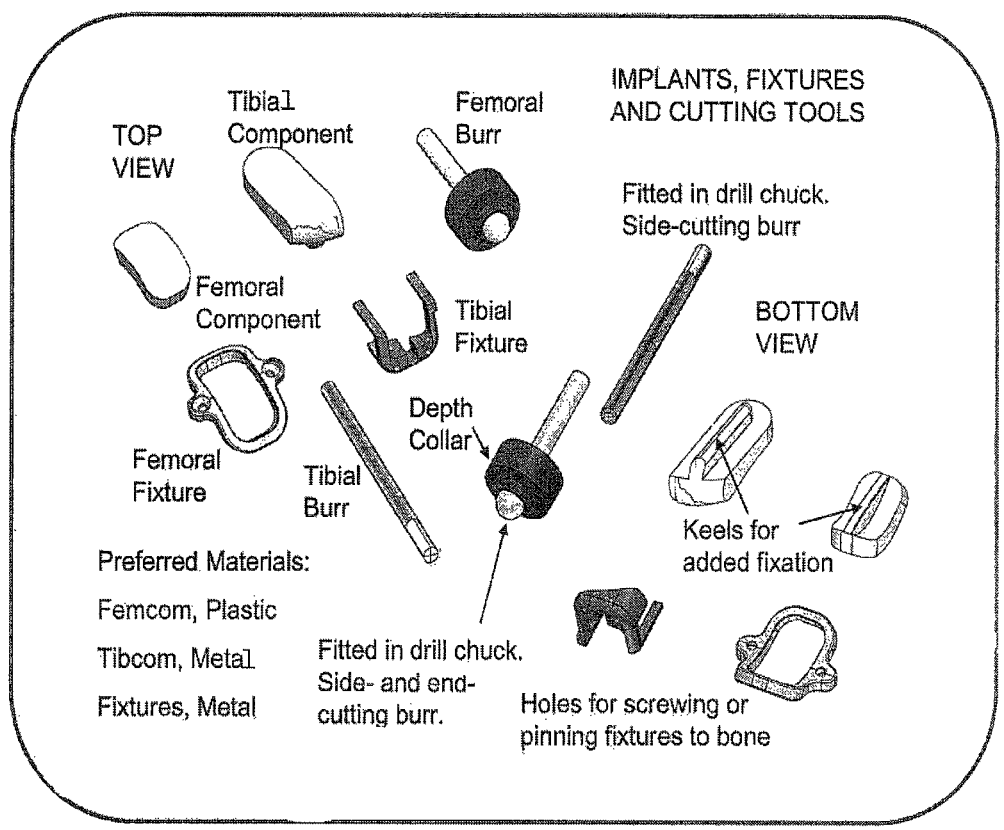
FIG. 14 depicts a surgical kit in accordance with an embodiment of the invention.

FIG. 14 illustrates an embodiment of the invention where the femoral and tibial implants are provided as a kit, including various femoral and tibial frames and fixture systems, cutting guides and surgical burrs. The kit further includes sterile packaging and instructions for use.

If an isolated metallic tibial plateau is used, the bearing surface should be shaped to give maximum conformity with the femoral condyles. In practice this means that there would be conforming surfaces in early flexion, but less conformity in flexion due to the diminishing sagittal radius of the medial femoral condyle. There is not the benefit, as in the intact knee, of a meniscus that can change its shape according to the shape of the femoral condyle itself. A conforming metallic component can be even more rigid fixation to the tibia than a shallow component, because of the high shear and tilting forces that are likely to occur. Another consideration for the shape of the upper surface of a metallic tibial plateau is the required stability on the one hand, and freedom of motion on the other hand. In the intact knee on the medial side, there are only a few millimeters of AP laxity at all angles of flexion due to the actions of the cruciate ligaments, further augmented. On the medial side, the stability is further augmented by the dishing of the tibial surface, the menisci, and the medial collateral ligament. Hence from this point of view, the medial dishing of a metallic plateau is an advantage regarding wear of the medial femoral condyle. Overall however, for durability and absence of pain, replacement bearing surfaces can be done for both the femur and tibia, and each would need to be rigidly fixed to the bone. For kinematic compatibility, the contours of the artificial surfaces should closely match those of the original femur.

For the treatment of the medial compartment in early OA, where the cruciate ligaments are intact or if adapted in cases where the anterior cruciate is damaged, and where there is no significant varus deformity, there is an additional aspect. A nonlimiting example of a typical knee which is suitable for this treatment is one where the arthritic lesions are localized on the distal medial femoral condyle, and on the central or anterior regions of the medial tibial plateau. The lateral side of the joint is able to sustain normal weight-bearing while the patello-femoral joint shows only slight arthritic lesions at most such that there is no significant pain deriving from that compartment. The patients benefiting are those who still are pursuing an active lifestyle, with a typical age range from 50-65 years. The procedure is envisaged as performed through small incisions and involve much less trauma than a standard total knee replacement, and even less trauma than a standard unicompartmental knee replacement.

The femoral implant can have various widths, such as 12 mm, 16 mm, or 20 mm width; and various thicknesses, such 6 or 8 mm. Different materials can be used for the femoral implant, but preferably it is a plastic, such as ultra high molecular weight polyethylene (UHMWPE), or a more rigid polymer such as polyetheretherketone (PEEK).

In one embodiment, the femoral component is made from a wear-resistant polymer such as highly cross-linked polyethylene, with a thickness of at least 8 mm, an optional keel along the base 2-4 mm wide, where the component is inset into the femoral condyle leaving 2-4 mm of bone on each side. The component is sized to carry load from approximately 5 degrees hyperextension to approximately 40-60 degrees flexion. It is flush with the cartilage at the anterior and posterior locations, and projects 0.5-1 mm above the cartilage in the center, the projection tapering down to zero at each end. The projection causes more of the weight-bearing to be in the component and less in surrounding cartilage at each side. The outer radii of the femoral component in the frontal plane, is about 1-3 mm smaller than that of the tibial component for moderately close conformity and stability. The lower surface of the component can be designed for osseointegration. All edges have a small radius, such as 0.5 mm, to avoid stress concentrations of the bone interfacing with the component.

An advantage of making the femoral component in a polymer is that the tibial component can be made from metal. A metal implant can be made thinner, thus requiring less tibial bone resection. However there are alternate material choices. A molded polyethylene can be used, or a stiff polymer such as polyetheretherketone (PEEK). It is possible to make the femoral component from metal, interfacing with polymer on the tibial side. These are the materials conventionally used today for unicompartmental replacements.

The implant can be fixed to the bone with polymethylmethacrylate cement (PMMA), which is commonly used in knee replacements. Another method is to bond a layer of a porous material such as porous tantalum to the base of the plastic component and rely on subsequent bone ingrowth. The lower surface could also be fused with a trabecular metal for ingrowth fixation. The side and lower surfaces can have grooves to help the bonding.

The tibial implants can have one of several different forms and can have several different shapes. A slot is cut into the tibia from the anterior side, and the implant is introduced anteriorly. The implant is assumed to be bonded to bone (after ingrowth) but not to cartilage. As shown, the device can have different thicknesses, such as 6 mm or 8 mm, can use a single keel or a dual keel for support (1.5-2.5 mm wide and 4-8 mm deep, with lower surface is designed for osseointegration), and can have a width from about 12 to 24 mm, including widths of 10, 12, 14, 16, 20, and 24 mm, or more typically, about 16-24 mm in width. The implant should have a thickness of 2-4 mm at its thinnest point, although higher thicknesses are available, such as 4-10 mm to cope with prevailing bone loss and deformity.

The tibial component can be made from a metal alloy, such as a Co—Cr alloy or a surface hardened titanium alloy, or from a ceramic. The tibial component is inset with 2-4 mm peripheral boundary of cartilage, and with meniscus preserved if applicable, where the bone preparation and component insertion is carried out from the anterior. Although not shown in FIG. 4, the upper surface can be dished with a radius of 50-90 mm, or 60-90 mm, in the sagittal plane to limit the anterior-posterior (AP) displacements and provide AP stability, and a similar dishing in the frontal plane to limit medial-lateral displacements and provide stability, particularly at the interior to match the intercondylar eminence of the anatomic knee. The radius can be about 60 mm anteriorly and 90 mm posteriorly. The top surface can have a high polish for low friction and wear.

The tibial component can be made from different materials. If the femoral component is made from metal, the tibial component can be made from a polymer, such as cross-linked polyethylene or molded polyethylene. It can also have a metal backing to provide greater rigidity and reduce the deformation of the polymer.

The fixation including PMMA or a porous surface, as well as the rounding of corners, as are used for the femoral component. Also, similar to the femoral component, all edges of the tibial component have a small radius to avoid stress concentrations.

The inserted tibial component is compatible with preserving the meniscus, which is released anteriorly to allow access to the component. The tibia component can come in different sizes and shapes. The dimensional variables are the sagittal radii, the AP length and the ML width. The component is preferably made from a metal, such as Co—Cr alloy. Fixation can be with acrylic cement, or with a fused-in porous material. The thickness of tibial component at the center is about 2-3 mm. The tibial component is fixed, ensuring that the boundaries are flush or slightly recessed relative to the surrounding cartilage surfaces (step i). As shown here, the tibial implant is generally elongated with one end rounded and an opposite end designed to conform to the shape of the tibia.

The compressive stresses and strains on the bone at the base of the recess were calculated using finite element analysis for the normal anatomic knee, and for the different versions of the femoral and tibial components. The criterion was that the strains were the baseline against which to compare the strains after implantation. If the strains were higher, that would imply that there was a possibility of compressive bone failure, which would impair the fixation and durability of the implant. On a comparative basis, implants with lower strains are preferred, all else being equal. The strains for the anatomic knee were less than for all of the implants analyzed, including on the femur and tibia. The strains were approximately inversely proportional to width.

For the femur, the strains were similar whether plastic or metal was used, for both 6 mm and 8 mm thick components. For the tibia, there was some advantage to using metal for the thinner component. For the tibia, there was a major reduction of stresses using a keel. Using two keels produced a further significant decrease. Rounding the edges of the components, including the keels, avoided stress concentrations at those locations. By insetting components, versus seating on a straight-across resection, was in transmitting shear stresses were transmitted down the peripheral bone contact, hence reducing the strains on the lower surface of the bone.

Methods of making a patient-specific knee implant set are included in the scope of the invention. This is accomplished by first imaging the knee of a patient having a degenerative knee condition thereby creating one or more three-dimensional maps of the femoral and tibial surfaces of the patient. Standard imaging techniques such as MRI and CT scans permit accurate high-resolution maps of the patient's anatomy, and specifically allow determination of the degree of condyle curvature as well as patient-specific anatomic variations that are within the resurfacing areas. Using standard computer systems with appropriate software, these patient maps are rendered as three-dimensional virtual models of the patient's tibia and femur. Systems exist for patient-specific total knee replacement procedures, such as the Signature™, Visionaire™ and ConforMIS™ systems, and the present invention utilizes similar mapping and rendering technologies. Essentially, the patient specific femoral and tibial maps are provided to a computer system, the computer system having software for rendering the femoral and tibial maps into a 3-dimensional virtual model of the femur and tibia of the patient. The femoral and tibial subregions defining femoral and tibial implant locations are determined from the virtual model. From such models, a femoral and/or a tibial implant is created such that the exterior surfaces of the femoral and/or the tibial implant substantially conforms to the shape of a native femoral condyle or a native tibial surface, respectively. Creation of the implant can be achieved through molding techniques or by direct sculpting techniques, or a combination of these. Patient-specific tibial surgical cutting guides or a patient-specific femoral surgical cutting guide sets are similarly created from the 3-dimensional virtual model.

We claim:

1. A tibial resurfacing implant, comprising:
   a tibial implant structure having a single dished morphology that is characterized with respect to a coordinate system including an x-axis, a y-axis and a z-axis as having a planar, tibia-facing surface at an end opposite to a femur-facing surface, wherein the tibial implant structure extends in a direction of the y-axis between the femur-facing surface that extends transverse to the y-axis and is bounded by a femur-facing periphery, and the planar tibia-facing surface that extends transverse to the y-axis and is bounded by a tibia-facing periphery, wherein the tibial implant structure has a perimeter surface extending between the femur-facing periphery and the tibia-facing periphery, wherein the perimeter surface includes:
   i. a planar portion extending transverse to the z-axis and bounded by a first portion of the tibia-facing periphery, a first portion of the femur-facing periphery, a first lateral edge and a second lateral edge, and
   ii. an annulus-like perimeter surface portion extending in part, about the y-axis and bounded by a second portion of the tibia-facing periphery, a second portion of the femur-facing periphery, the first lateral edge and the second lateral edge, and wherein the annulus-like perimeter surface portion is configured to conform substantially to a perimeter of a tibia;
   wherein the femur-facing surface is characterized by the single dished morphology;
   wherein the planar, tibia-facing surface includes a keel extending therefrom in a direction substantially parallel to the planar portion of the perimeter surface; and
   wherein the tibial implant structure varies in thickness in the direction of the y-axis at one or more regions whereby the planar portion of the perimeter surface and the planar tibia-facing surface are configured to conform to respective slopes of a medial tibial bone resection in frontal and sagittal planes,
     the planar tibia-facing surface tapering downward medially in the frontal plane relative to a first plane that is substantially perpendicular to a second plane that is substantially parallel to the keel, such that a medial end region of the tibial implant structure is thicker than a lateral end region,
     and tapering downward posteriorly in the sagittal plane such that a posterior end region of the tibial implant structure is thicker than an anterior end region,
     wherein the planar, tibia-facing surface has a greater taper downward posteriorly in the sagittal plane than downward medially in the frontal plane.

2. The tibial implant of claim 1, the planar, tibia-facing surface being non-perpendicular to the keel.

3. The tibial implant of claim 1, the keel including a cylindrical portion extending from an anterior end of the keel to a posterior end of the keel, the diameter of the cylindrical portion at the anterior end of the keel approximating the diameter of the cylindrical portion at the posterior end of the keel.

4. The tibial implant of claim 3, the cylindrical portion having annular notches or extrusions.

5. The tibial implant of claim 4, the cylindrical portion having annular notches or extrusions between 0.1 and 0.2 mm relative to the diameter of the cylindrical portion.

6. The tibial implant of claim 3, the diameter of the cylindrical portion at the anterior end of the keel being greater than the diameter of the cylindrical portion at the posterior end of the keel.

7. The tibial implant of claim 3, wherein a distance between the tibial-facing surface and cylindrical portion at the posterior end of the keel is greater than a distance between the tibial-facing surface and the cylindrical portion at the anterior end of the keel.

8. The tibial implant of claim 7, wherein a difference between the distance between the tibial-facing surface and cylindrical portion at the anterior end of the keel and the distance between the tibial-facing surface and the cylindrical portion at the posterior end of the keel is between about 0.2 mm and 0.5 mm.

9. The tibial implant of claim 3, further comprising one or more coated regions.

10. The tibial implant of claim 1, the planar, tibia-facing surface tapering downward posteriorly in the sagittal plane at an angle between about 3 degrees and about 8 degrees.

11. The tibial implant of claim 1, which is a one-piece implant.

12. The tibial implant of claim 1, the tibial-facing surface being textured.

13. The tibial implant of claim 1, having a thickness of 5 mm or less at its thinnest point along the y-axis of the structure.

14. The tibial implant of claim 1, wherein the implant is configured to conform to the medial tibial bone resection having a medial slope in the frontal plane of between about 3 and about 8 degrees.

15. The tibial implant of claim 1, wherein the implant is configured to conform to the medial tibial bone resection having a posterior slope in the sagittal plane of between about 3 and about 8 degrees.

16. The tibial implant of claim 1, comprising at least one of cobalt chrome alloy, titanium alloy and ceramic.

17. A knee implant set, comprising: in combination, the tibial resurfacing implant of claim 1 and a femoral resurfacing implant.

18. The tibial implant of claim 1, wherein a portion of the annulus-like perimeter surface portion and the planar tibia-facing surface intersect at the second portion of the tibia-facing periphery at an angle less than 90 degrees.

19. The tibial implant of claim 1, wherein the planar, tibia-facing surface tapers downward medially in the frontal plane at an angle between about 3 degrees and about 8 degrees.

20. The tibial implant of claim 1, wherein the planar, tibia-facing surface tapers downward medially in the frontal plane at an angle of 5 degrees.

21. The tibial implant of claim 1, wherein the planar, tibia-facing surface tapers downward posteriorly in the sagittal plane at an angle of 7 degrees.

22. The tibial implant of claim 1, wherein the planar, tibia-facing surface tapers downward medially in the frontal plane at an angle of 5 degrees and downward posteriorly in the sagittal plane at an angle of 7 degrees.

23. The tibial implant of claim 1, wherein the planar, tibia-facing surface tapers downward medially in the frontal plane at an angle that is based on a determined varus tilt of the tibia.

* * * * *